(12) United States Patent
Romanytsia

(10) Patent No.: US 12,253,502 B2
(45) Date of Patent: Mar. 18, 2025

(54) METHOD AND SYSTEM FOR CALIBRATING A NON-SELECTIVE CHEMICAL SENSOR

(71) Applicant: ELLONA, Toulouse (FR)

(72) Inventor: Ivan Romanytsia, Toulouse (FR)

(73) Assignee: ELLONA, Toulouse (FR)

( * ) Notice: Subject to any disclaimer, the term of this patent is extended or adjusted under 35 U.S.C. 154(b) by 320 days.

(21) Appl. No.: 17/758,346

(22) PCT Filed: Feb. 1, 2021

(86) PCT No.: PCT/EP2021/052288
§ 371 (c)(1),
(2) Date: Jul. 1, 2022

(87) PCT Pub. No.: WO2021/156193
PCT Pub. Date: Aug. 12, 2021

(65) Prior Publication Data
US 2023/0003703 A1     Jan. 5, 2023

(30) Foreign Application Priority Data
Feb. 7, 2020   (FR) ...................................... 2001251

(51) Int. Cl.
*G01N 33/00*     (2006.01)
(52) U.S. Cl.
CPC ................................ *G01N 33/0006* (2013.01)
(58) Field of Classification Search
CPC .................................................. G01N 33/0006
See application file for complete search history.

(56) References Cited

U.S. PATENT DOCUMENTS

| | | | | |
|---|---|---|---|---|
| 7,532,992 B2* | 5/2009 | Liescheski | ............. | G01D 3/022 702/100 |
| 7,711,493 B2* | 5/2010 | Bartkowiak | ....... | A61B 5/14532 436/95 |

(Continued)

FOREIGN PATENT DOCUMENTS

| | | | | |
|---|---|---|---|---|
| CN | 101854907 A | * | 10/2010 | ............. A61P 43/00 |
| EP | 2327984 A2 | | 6/2011 | |
| WO | WO 2006063094 A1 | * | 6/2006 | ........... G01N 21/359 |

OTHER PUBLICATIONS

International Search Report and Written Opinion on corresponding PCT application (PCT/EP2021/052288) from International Searching Authority (EPO) dated Apr. 30, 2021.

*Primary Examiner* — Tung S Lau
(74) *Attorney, Agent, or Firm* — Alumen IP Law PC

(57) ABSTRACT

Disclosed is a method for calibrating a sensor to be calibrated by means of a reference sensor, the sensor to be calibrated being configured to determine a chemical signal based on a conversion function for converting an electrical signal, the reference sensor being configured to determine a reference signal, the method having: • measuring, during a reference time period, a first chemical signal (S1P1) and a first reference signal (S2P1) and, during a test period, a second chemical signal (S1P2) and a second reference signal (S2P2), • determining regression functions (gP1, gP2) defined as follows: S2P1=gP1(S1P1) and S2P2=gP2(S2P2), • calculating a difference between the regression functions (gP1, gP2) and • when the difference is greater than a reference difference, determining an optimized conversion function.

10 Claims, 4 Drawing Sheets

(56) References Cited

U.S. PATENT DOCUMENTS

| | | | |
|---|---|---|---|
| 2007/0174013 A1* | 7/2007 | Liescheski | G01F 23/18 |
| | | | 702/85 |
| 2009/0156924 A1 | 6/2009 | Shariati et al. | |
| 2009/0192751 A1 | 7/2009 | Kamath et al. | |
| 2009/0216477 A1* | 8/2009 | Liescheski | G01F 23/18 |
| | | | 702/100 |
| 2015/0164384 A1* | 6/2015 | Varsavsky | G01N 27/3274 |
| | | | 600/316 |
| 2021/0330219 A1* | 10/2021 | Ma | G01N 33/66 |

\* cited by examiner

METHOD AND SYSTEM FOR CALIBRATING A NON-SELECTIVE CHEMICAL SENSOR

TECHNICAL FIELD

The present invention relates to the field of calibration of a non-selective chemical sensor.

The selectivity of a chemical sensor is defined by its ability to determine a chemical signal of the amount of a single chemical compound in a chemical medium to the exclusion of others. A chemical compound is distinguished from another chemical compound on the one hand by its type, that is, its chemical composition, and on the other hand by its nature, that is, its physicochemical properties.

In a known manner, a non-selective chemical sensor, such as a semiconductor sensor, is configured to determine a measurement signal of the amount of a group of chemical compounds of a chemical medium, such as the concentration of volatile organic compounds, abbreviated as "VOC", in the air. Examples of VOCs are pollutants emitted by means of transport, printers, radiators, smoking, candle burning or emissions from ripening fruit and vegetables. For this, a semiconductor sensor, also called a "MOX sensor" or "MOS sensor", comprises a metal oxide layer heated by a heating element on which VOCs are fixed, this phenomenon being known to the skilled person under the term "adsorption". Such a semiconductor sensor further comprises electrodes for measuring the electrical conductivity of the metal oxide layer, which is a function of the amount of adsorbed VOCs, which makes it possible to determine the concentration of VOC in the air based on a conversion function specific to the semiconductor sensor. The determination of the concentration of VOC in the air can be used, in particular, to measure the quality of the indoor air in an office, a home, a school or a fruit and vegetable packaging and/or ripening area, or to measure the quality of the outdoor air near a transportation route, such as a road or an airport.

In a known manner, a non-selective chemical sensor has to be calibrated before its first use. To do this, using the previous example of the semiconductor sensor, the semiconductor sensor is placed in several standard media with known concentration of VOC. The deviation between the measured concentration of VOC by the semiconductor sensor and the theoretical concentration of VOC of each standard medium is corrected by adjusting the conversion function between the electrical conductivity and the concentration of VOC specific to the semiconductor sensor.

In practice, the response of a semiconductor sensor drifts during its use, especially because of the gradual obstruction of the pores of the metal oxide layer due to the adsorption of VOCs which modifies its electrical conductivity. Such a semiconductor sensor has to be regularly calibrated to ensure that the measured concentration of VOC remains reliable and accurate. This requires uninstalling the semiconductor sensor to place it in standard media and then reinstalling said semiconductor sensor in the office, which is time consuming. In addition, if there is an oversight or delay in performing the calibration or an unforeseen malfunction of the semiconductor sensor, a biased concentration of VOC may be unknowingly measured.

The invention is thus directed to a method and system for calibrating a non-selective chemical sensor that eliminates at least some of these drawbacks.

SUMMARY

The invention relates to a method for calibrating at least one non-selective chemical sensor, called a "sensor to be calibrated", by means of at least one reference sensor, said sensor to be calibrated and said reference sensor being in contact with a same chemical medium, said sensor to be calibrated being configured to determine a chemical signal of the amount of a group of chemical compounds in said chemical medium, said reference sensor being configured to determine a reference signal whose temporal variation is correlated to that of said chemical signal, said sensor to be calibrated comprising:
- an element for measuring an electrical signal, which is a function of the amount of said group of chemical compounds in said chemical medium, and
- an element for calculating said chemical signal based on a conversion function f specific to said sensor to be calibrated and configured to associate the corresponding chemical signal S1 with said measured electrical signal U according to the following relationship: $S1=f(U)$.

The invention is remarkable in that the method comprises:
- a step of measuring, during a reference period, a first chemical signal $S1_{P1}$ by means of the sensor to be calibrated and a first reference signal $S2_{P1}$ by means of the reference sensor,
- a step of determining a first regression function $g_{P1}$ defined as follows: $S2_{P1}=g_{P1}(S1_{P1})$,
- at least one step of measuring, during a test period subsequent to the reference period, a second chemical signal $S1_{P2}$ by means of the sensor to be calibrated and a second reference signal $S2_{P2}$ by means of the reference sensor,
- at least one step of determining a second regression function $g_{P2}$ defined as follows: $S2_{P2}=g_{P2}(S_{P2})$,
- at least one step of calculating a deviation between the first regression function and the second regression function and
- when the deviation is greater than a reference deviation, at least one step of determining an optimized conversion function so that the second regression function is substantially equal to the first regression function, so as to calibrate the sensor to be calibrated.

By virtue of the invention, a non-selective chemical sensor can be calibrated directly during the acquisition of measurements of interest, that is, in the chemical medium whose amount of a group of chemical compounds is to be determined. It is therefore not necessary to place the sensor to be calibrated in one or more standard media of known chemical composition. The calibration is thus simpler, faster and more convenient to implement, but also more relevant because it is performed directly in the chemical medium of interest.

Such a calibration method is also reliable because it is based on comparisons of measurements of the sensor to be calibrated and of a reference sensor acting as a standard sensor, whose measurements are considered valid and temporally correlated to the measurements of the sensor to be calibrated. Each comparison is also made on the basis of measurements made over the same period of time and in the same chemical medium, which increases reliability. Furthermore, such a calibration method is accurate because the first comparison is performed during a reference period when a measurement of the non-selective chemical sensor is deemed valid, in the manner of a calibration phase. The comparison during a test period is further repeatable when and as often as desired, for example periodically.

According to one aspect, the calibration method is implemented for a single sensor to be calibrated and a single reference sensor. Such a method is configured to calibrate a single sensor.

According to another aspect, the calibration method is implemented for a plurality of sensors to be calibrated and at least one reference sensor, each sensor to be calibrated being calibrated by means of a single reference sensor, preferably identical for all sensors to be calibrated. Such a method is suitable for the calibration of a sensor array. The use of a single reference sensor advantageously makes it possible to limit the overall size.

According to one aspect of the invention, the calibration method is implemented for a plurality of test periods subsequent to the reference period, said method comprising for each test period:
- a step of measuring, during the test period, a second chemical signal $S1_{P2}$ by means of the sensor to be calibrated and a second reference signal $S2_{P2}$ by means of the reference sensor,
- a step of determining a second regression function $g_{P2}$ defined as follows: $S2_{P2}=g_{P2}(S1_{P2})$,
- a step of calculating a deviation between the first regression function and the second regression function and when the deviation is greater than a reference deviation,
- a step of determining an optimized conversion function so that the second regression function is substantially equal to the first regression function, so as to calibrate the sensor to be calibrated.

Advantageously, the first regression function calculated for the reference period does not have to be recalculated, thus saving time. The first regression function thus serves as a control for all subsequent test periods, which makes the method reliable and accurate, as the optimized conversion function is always obtained based on the same first regression function. Furthermore, such a calibration method can thus easily be reproduced many times, preferably periodically to prevent drift of the sensor to be calibrated.

According to one aspect of the invention, the sensor to be calibrated is in the form of a VOC sensor, in order to perform measurements of pollutants in the air.

Preferably, the sensor to be calibrated is in the form of a semiconductor sensor or an electrochemical sensor or a photoionization sensor. The choice of the nature of the sensor is advantageously made according to the chemical compounds whose amount is to be measured. To measure an amount of various chemical compounds, a semiconductor sensor represents an economic and accurate solution. To measure an amount of more targeted chemical compounds, an electrochemical sensor represents a reliable and accurate solution. To measure an amount of ionizable chemical compounds, a photoionization sensor is more suitable and accurate.

According to one aspect of the invention, the reference sensor is in the form of a carbon dioxide sensor, in order to measure the amount of carbon dioxide in an occupied enclosed space, this amount being advantageously correlated to the occupancy of the space, and thus to the amount of VOCs emitted into said space. Preferably, the reference sensor is in the form of a non-dispersive infrared sensor, known by the abbreviation "NDIR".

According to another aspect of the invention, the reference sensor is in the form of a sound intensity sensor, in order to measure, for example, the noise emitted in proximity to a road, this noise advantageously being correlated to the traffic on the road, and thus to the amount of VOCs emitted by said traffic on the road.

Preferably, the reference sensor is in the form of a self-calibrated sensor, whose measurements are advantageously valid at any time and do not drift during its use. A self-calibrated reference sensor thus forms a reliable and accurate standard sensor for both the reference period and the test period(s).

According to one aspect, the reference period is between one day and one month, preferably in the order of one week. Preferably, the test period is between one day and one month, preferably in the order of one week, more preferably equal to the reference period. Advantageously, such a reference period and such a test period are long enough to characterize the full range of variation in the amount of chemical compounds in the chemical medium, and short enough to limit data storage.

According to one preferred aspect, the first chemical signal comprises a plurality of measurement points spaced apart by a measurement pitch between 1 min and 4 h, preferably in the order of 1 h. Preferably, the first reference signal comprises a same number of measurement points as the first chemical signal and spaced by the same measurement pitch. Also preferably, the second chemical signal comprises a plurality of measurement points spaced apart by a measurement pitch between 1 min and 4 h, preferably in the order of 1 h. Preferably, the second reference signal comprises a same number of measurement points as the second chemical signal and spaced by the same measurement pitch. Advantageously, the obtained regression functions comprise sufficient points to be representative and accurate, while limiting data storage.

Preferably, the first regression function is polynomial, preferably affine, more preferably linear. Also preferably, the second regression function is polynomial, preferably affine, more preferably linear. Such regression functions are advantageously simple to determine and operate.

According to one aspect of the invention, the deviation holds the following relationship: $\varepsilon=\text{Max}(IS1_{P1}-S1_{P2}I)/S1_{P1}$ such that $S2_{P1}=S2_{P2}$. Such a deviation is advantageously simple to determine and representative of the possible drift of the sensor to be calibrated.

Preferably, the reference deviation is between 0.01 and 0.1, preferably in the order of 0.05, which makes it possible to avoid any significant drift while avoiding having to carry out an irrelevant micro-correction.

According to one aspect of the invention, the second chemical signal $S2_{P2}$ being determined based on a second electrical signal $U_{P2}$, the optimized conversion function $f^*$ holds the following relationship: $g_{P2}(f^*(U_{P2}))=G_{P1}(S1_{P1})$. Such an optimized conversion function makes it possible to calibrate the sensor in such a way that for a given amount of chemical compounds, the sensor to be calibrated provides the same chemical signal as during the reference period.

The invention also relates to a calibration system for implementing the calibration method as previously described, said system comprising at least one non-selective chemical sensor, called a "sensor to be calibrated", and at least one reference sensor configured to be in contact with a same chemical medium, and a calculation module connected to the sensor to be calibrated and to the reference sensor, said sensor to be calibrated being configured to determine a chemical signal of the amount of a group of chemical compounds in said chemical medium, in particular a first chemical signal $S1_{P1}$ during a reference period and a second chemical signal $S1_{P2}$ during a test period, said reference sensor being configured to determine a reference signal whose temporal variation is correlated to that of said chemical signal, in particular a first reference signal $S2_{P1}$ during said reference period and a second reference signal $S2_{P2}$ during said test period, said sensor to be calibrated comprising:

an element for measuring an electrical signal, which is a function of the amount of said group of chemical compounds in said chemical medium, and an element for calculating said chemical signal based on a conversion function f specific to said sensor to be calibrated and configured to associate the corresponding chemical signal S1 with said measured electrical signal U according to the following relationship: S1=f (U), said calculation module being configured to:

determine a first regression function $g_{P1}$ and a second regression function gp2 defined as follows: $S2_{P1}=g_{P1}(S1_{P1})$ and $S2_{P2}=g_{P2}(S1_{P2})$ calculate a deviation between the first regression function and the second regression function and when the deviation is greater than a reference deviation, determine an optimized conversion function so that the second regression function is substantially equal to the first regression function, so as to calibrate the sensor to be calibrated.

Advantageously, such a calibration system is space-saving and can be easily and conveniently installed directly in the physical medium being measured by the sensor to be calibrated. Such a calibration system thus does not require moving the sensor to be calibrated or human intervention, thus saving time and human resources.

According to one aspect, the calibration system comprises a single sensor to be calibrated and a single reference sensor. According to another aspect, the calibration system comprises a plurality of sensors to be calibrated and at least one reference sensor, each sensor to be calibrated being calibrated using a single reference sensor, preferably identical for all sensors to be calibrated. Such a calibration system advantageously allows the calibration of an array of sensors, preferably with a single reference sensor in order to limit the overall size.

The invention also relates to a computer program implementing the calibration method as previously described.

BRIEF DESCRIPTION OF THE DRAWINGS

The invention will be better understood upon reading the following description, which is given solely by way of example, and refers to the attached drawings given as non-limiting examples, in which identical references are given to similar objects and in which.

It should be noted that the figures set forth the invention in detail for implementing the invention, said figures may of course be used to better define the invention where appropriate.

DETAILED DESCRIPTION

Figure 1:
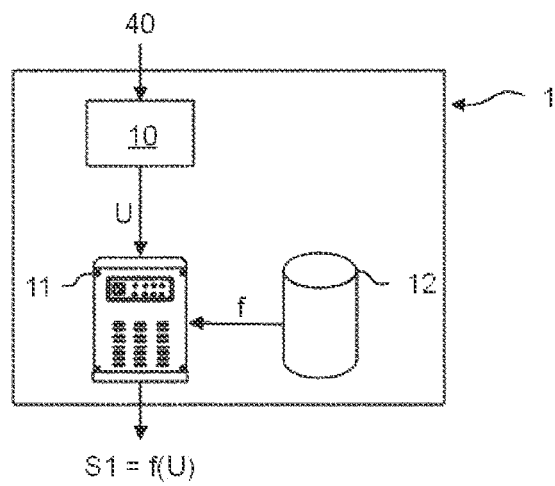
FIG. 1 is a functional schematic representation of a sensor to be calibrated.

In a known manner and with reference to FIG. 1, a non-selective chemical sensor 1 is configured to determine a chemical signal S1 of the amount of a group of chemical compounds 40 in a chemical medium. Here, the selectivity of a chemical sensor is defined by its ability to determine a chemical signal of the amount of a single chemical compound in a chemical medium to the exclusion of the others. A chemical compound is distinguished from another chemical compound on the one hand by its type, that is, its chemical composition, and on the other hand by its nature, that is, its physicochemical properties.

Still with reference to FIG. 1, a non-selective chemical sensor 1 comprises:

an element for measuring 10 an electrical signal U, which is a function of the amount of the group of chemical compounds 40 in the chemical medium, and an element for calculating 11 the chemical signal S1 based on a conversion function f configured to associate the corresponding chemical signal S1 with the measured electrical signal U according to the following relationship: S1=f(U). The conversion function f is specific to the sensor 1 and comes from a database 12 which may or may not be integrated in the calculation element 11.

Figure 2:
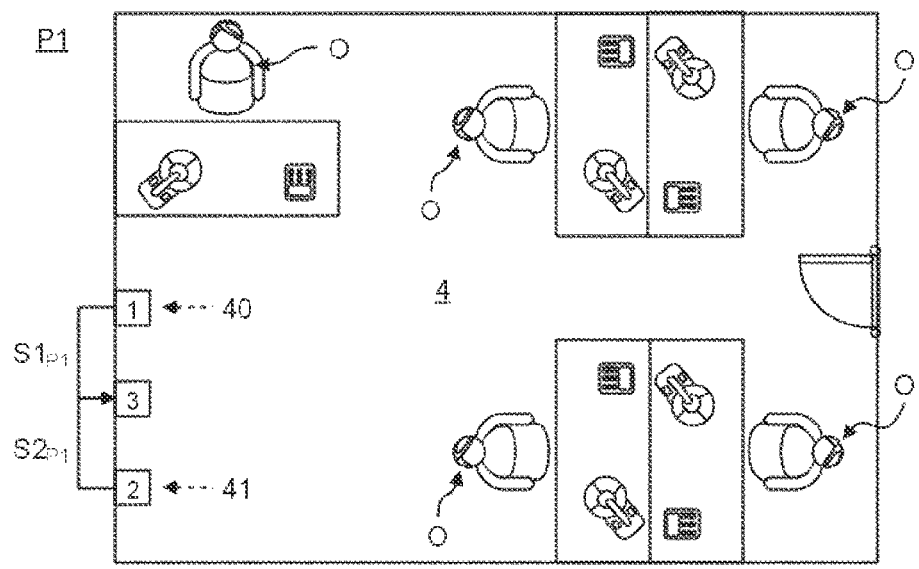
FIG. 2 is a functional schematic representation of a system for calibrating the sensor to be calibrated of FIG. 1 according to an embodiment of the invention and during a reference period.
Figure 3:
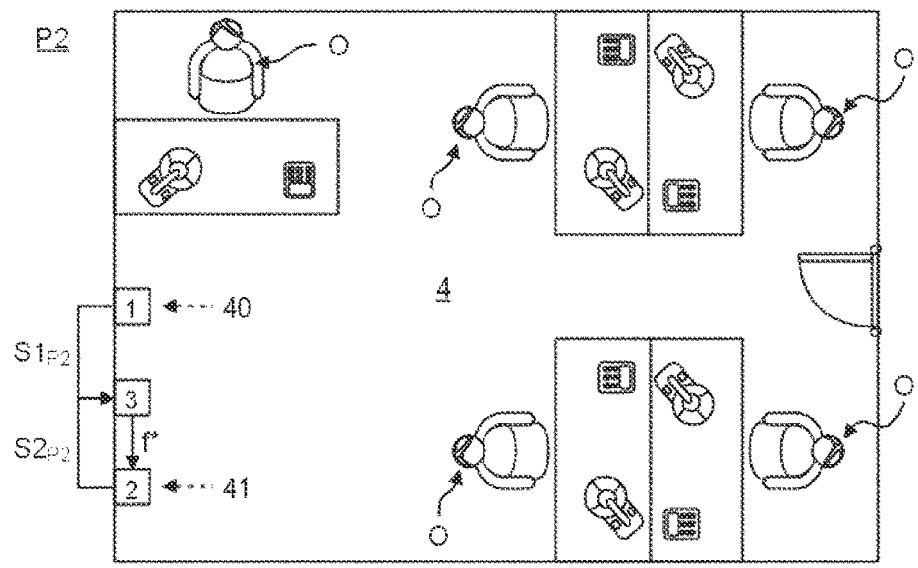
FIG. 3 is a functional schematic representation of the calibration system of FIG. 2, during a test period.

As an example of a non-selective chemical sensor, a semiconductor sensor 1, also referred to as a "MOX sensor" or "MOS sensor", configured to determine the concentration S1 of volatile organic compounds 40, abbreviated as "VOCs", in the indoor air of an office 4, as illustrated in FIGS. 2 and 3, will be considered hereafter. Such a semiconductor sensor 1 comprises a measurement element 10 comprising a metal oxide layer, a heating element and measurement electrodes. The metal oxide layer is heated by the heating element so that VOCs 40 are fixed thereto, a phenomenon known to the skilled person under the term "adsorption". The measurement element 10, and more precisely the measurement electrodes, is configured to measure an electrical conductivity U of the metal oxide layer, which is a function of the amount of adsorbed VOCs and forms the electrical signal. A chemical signal in the form of a concentration S1 of VOC 40 is then determined based on the measured electrical conductivity U via the conversion function f.

In a known manner, the response of a semiconductor sensor 1 drifts during its use, especially because of the gradual obstruction of the pores of the metal oxide layer due to the adsorption of VOCs 40 which modifies the measured electrical conductivity U. In other words, the electrical conductivity U measured at several months intervals under identical conditions is different, although the actual concentration of VOC is identical. The determined concentration S1 of VOC 40 is then biased because the conversion function f no longer reflects the relationship between the electrical conductivity U and the actual concentration of VOC 40 in the air of the office 4. It is therefore necessary to calibrate the semiconductor sensor 1 so that the measured concentration S1 of VOC 40 remains reliable and accurate. The calibration consists in correcting the conversion function f so that it compensates for the drift of the sensor 1, that is, so that it reflects the new relationship linking the electrical conductivity U and the actual concentration of VOC 40 in the air of the office 4.

The invention relates to a method for calibrating a semiconductor sensor 1 such as that previously described, or more generally any non-selective chemical sensor having a conversion function f to be calibrated, such as an electrochemical sensor or a photoionization sensor, hereinafter referred to as "sensor to be calibrated 1" for clarity.

Figure 5:
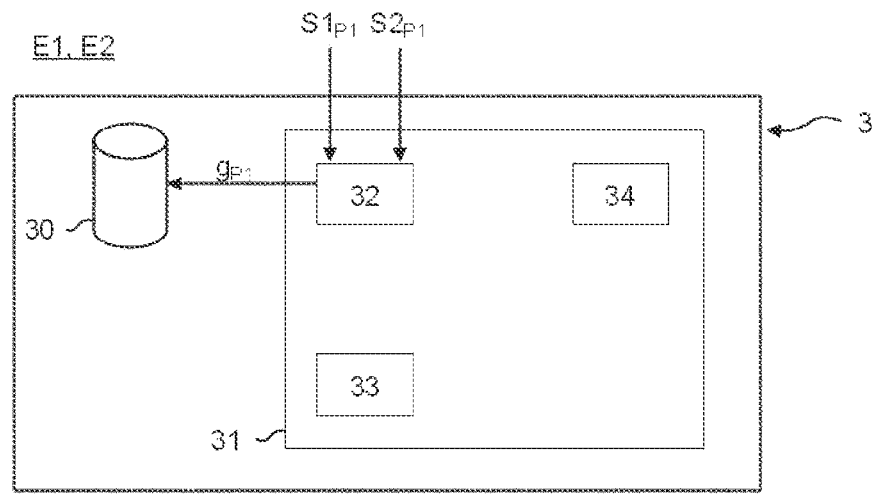
FIG. 5.
Figure 6:
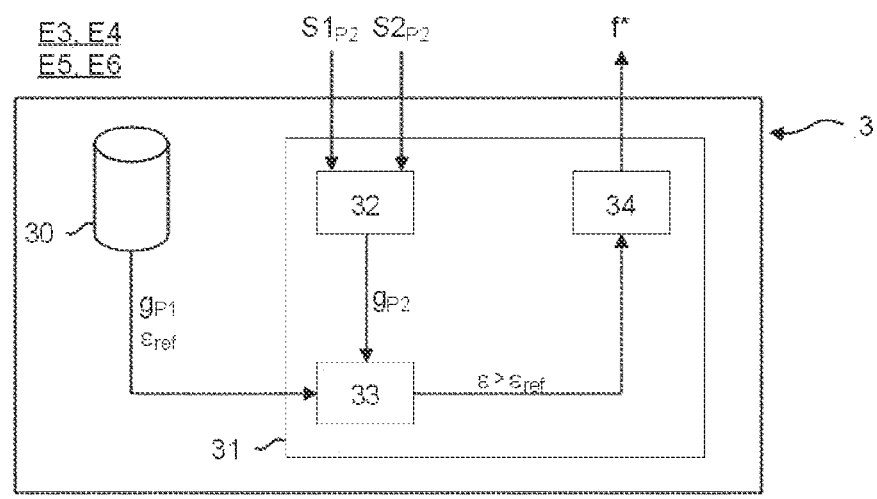
FIG. 6 are functional schematic representations of a calculation module of the calibration system of FIG. 2, respectively during the reference period and during the test period.

With reference to FIGS. 2 and 3, to implement the calibration method, the invention provides to use a calibration system comprising the sensor to be calibrated 1 and a reference sensor 2 different from the sensor to be calibrated 1 that is brought into contact with the same physical medium as the sensor to be calibrated 1, namely the indoor air of an office 4 in the example of FIGS. 2 and 3. The calibration system further comprises a calculation module 3 connected to the sensor to be calibrated 1 and to the reference sensor 2 and configured to compare their measurements in order to detect any drift of the sensor to be calibrated 1 and to calculate an optimized conversion function f*. Preferably, the calculation module 3 is in the form of a microprocessor. In the example of FIGS. 5 and 6, the calculation module 3 comprises a database 30 and a calculator 31 with three calculation units 32, 33, 34. Of course the calculation module 3 comprises any number of databases 30 integrated or not with the calculator 31 and any number of calculators 31 comprising any number of calculation units 32, 33, 34.

In order for the comparison to be relevant, the reference sensor 2 is chosen to be sensitive to a physicochemical quantity of the physical medium that is correlated to that of the sensor to be calibrated 1. In other words, the reference sensor 2 is configured to measure a reference signal S2 whose temporal variation is correlated to that of the chemical signal S1 measured by the sensor to be calibrated 1. Furthermore, the reference sensor 2 is preferably chosen to be selective and/or self-calibrated, so that its measurements are accurate and not subject to drift over time.

In the example of FIGS. 2 and 3, the reference sensor 2 is thus in the form of a carbon dioxide sensor 41, abbreviated as "CO2", configured to determine the concentration S2 of $CO_2$ 41 in the air of the office 4. Such a concentration S2 of $CO_2$ 41 is correlated to the concentration S1 of VOC 40 measured by the sensor to be calibrated 1 in that they are both related to the occupancy rate O of the office 4. Indeed, $CO_2$ 41 present in the office 4 is essentially emitted by the occupants of the office 4 and its temporal variation thus depends on the occupancy rate O of the office 4. VOCs 40 present in the office 4 are essentially emitted by the electronic devices such as computers, printers or radiators, used by the occupants, so that their temporal variation also depends on the occupancy rate O of the office 4. Furthermore, the reference sensor 2 is preferably in the form of a self-calibrated, non-dispersive infrared sensor selective to $CO_2$ 41.

Of course another reference sensor 2 could be chosen, the important thing being that it is configured to measure a reference signal S2 correlated to the chemical signal S1 of the sensor to be calibrated 1, accurate and not subject to drift. Thus, in this example, the reference sensor 2 could be sensitive to another physical quantity than $CO_2$ 41, such as oxygen which is essentially consumed by the occupants of the office 4 and whose amount is therefore correlated to that of VOC 40. However, $CO_2$ has the advantage of varying more in proportion relative to oxygen, which allows for more accurate calibration. Furthermore, in this example, the reference sensor 2 could be of a different nature, such as an electrochemical or non-dispersive infrared sensor, which has to be selective and self-calibrated. Thus, it should be noted that the choice of reference sensor 2 depends on the sensor to be calibrated 1, and especially on the group of chemical compounds 40 to which it is sensitive. In the example of FIGS. 2 and 3, the sensor to be calibrated 1 is sensitive to VOCs 40, but of course the sensor to be calibrated 1 could be sensitive to another group of chemical compounds 40.

Furthermore, preferably, the sensor to be calibrated 1 and the reference sensor 2 are installed in close proximity to each other, preferably adjacent to each other, so as to be in contact with a same physical medium 4 under identical physicochemical conditions. Preferably also, the calibration system forms a unitary module, which is easy to install, but of course the calculation module 3 could be remote to limit the overall size, since it does not require contact with the physical medium 4.

Figure 4:
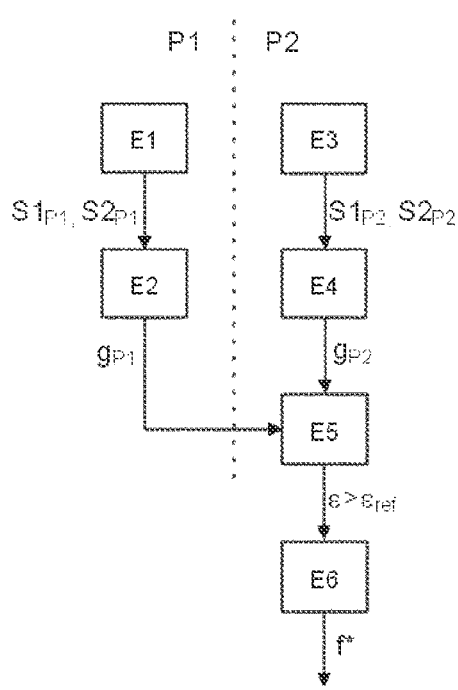
FIG. 4 is a schematic representation of the steps of a calibration method according to an embodiment of the invention.

A calibration method implemented by the previously described calibration system is described below. With reference to FIG. 4, the method comprises:

- a step of measuring E1, during a reference period P1 shown in FIG. 2, a first chemical signal $S1_{P1}$ by means of the sensor to be calibrated 1 and a first reference signal $S2_{P1}$ by means of the reference sensor 2,
- a step of determining E2 a first regression function $g_{P1}$ defined as follows: $S2_{P1} = g_{P1}(S1_{P1})$,
- a step of measuring E3, during a test period P2 illustrated in FIG. 3 and subsequent to the reference period P1, a second chemical signal $S1_{P2}$ by means of the sensor to be calibrated 1 and a second reference signal $S2_{P2}$ by means of the reference sensor 2,
- a step of determining E4 a second regression function $g_{P2}$ defined as follows: $S2_{P2} = g_{P2}(S1_{P2})$,
- a step of calculating E5 a deviation ε between the first regression function $g_{P1}$ and the second regression function $g_{P2}$ and
- when the deviation ε is greater than a reference deviation $\varepsilon_{ref}$ a step of determining E6 an optimized conversion function f* so that the second regression function $g_{P2}$ is substantially equal to the first regression function $g_{P1}$, so as to calibrate the sensor to be calibrated 1.

Advantageously, such a calibration method is performed in the physical medium and does not require moving the sensor to be calibrated 1 into one or more standard media as in prior art, thus saving time and resources. In addition, such a calibration method can be performed autonomously by the calibration system and in particular the calculation module in the form of a computer program, and therefore does not require human intervention as in prior art. The implementation of the calibration method in the physical medium also has the advantage of being more relevant, because the optimized conversion function f* is then specifically calculated for the medium of interest and the chemical compounds of interest. The accuracy of the calibration method is further guaranteed by the choice of the reference sensor 2, namely sensitive to a physical quantity whose temporal variation is correlated to that of the sensor to be calibrated. Preferably, the reference sensor 2 is also chosen to be selective and self-calibrated in order to provide accurate measurements that are not subject to drift.

Preferably, the calibration method is implemented for several test periods P2. More precisely, for each of the test periods P2, a measurement step E3, a determination step E4, a calculation step E5 and a determination step E6 are implemented. Advantageously, the calibration method is repeatable as often as desired. A regular or even periodic calibration, for example every three months, can thus be set up to periodically check the potential drift of the sensor to be calibrated 1 and correct it. Advantageously, such a calibration method guarantees the accuracy and reliability of the measurements of the sensor to be calibrated 1 as it is used. It should also be noted that regardless of the number of test periods P2, the measurement step E1 and the determination step E2 are only implemented once, thus also saving time and increasing the relevance of the calibration. Indeed, the first regression function $g_{P1}$ serves as a control and as a basis for comparison for the second regression function(s) determined subsequently.

Each of the steps of the calibration method is described in more detail below, considering only one test period P2. The steps are further described as part of the previously described calibration system, namely formed by a semiconductor sensor 1 of VOC 40 (that is the sensor to be calibrated), an infrared sensor 2 of CO2 41 (that is the reference sensor) and the calculation module 3, such as a microprocessor.

Figure 7:
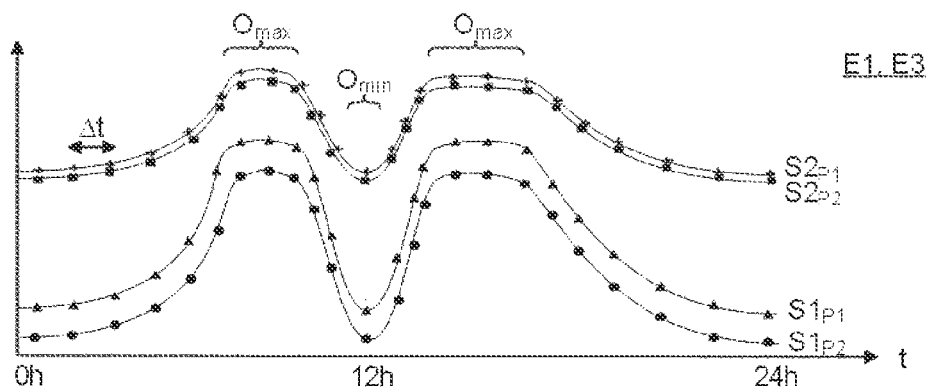
FIG. 7 is a representation of the physical signals of the sensor to be calibrated and of a reference sensor of the calibration system of FIG. 2, during the reference period and during the test period.

The calibration method starts with a step of simultaneously measuring E1 the concentration S1 of VOC 40 and the concentration S2 of CO2 41 of the indoor air of the office 4 illustrated in FIGS. 2 and 3. With reference to FIG. 7, the concentration S1 of VOC 40 is measured by the sensor to be calibrated during a reference period P1 and noted "first concentration S1P1 of VOC 40". The concentration S2 of CO2 41 of the indoor air of the office 4 is measured by the reference sensor 2 during the same reference period P1 and noted "first concentration S2P1 of CO2 41".

The reference period P1 is preferably chosen such that the response of the sensor to be calibrated 1 is deemed valid, that is, the sensor to be calibrated 1 is deemed calibrated and does not drift. In other words, the first concentration $S1_{P1}$ of VOC 40 is substantially identical to the actual concentration of VOC 40 of the indoor air in the office 4. In practice, the reference period P1 is chosen within days of the installation and/or configuration of the sensor to be calibrated 1 in the office 4. Alternatively, the reference period P1 is chosen within days of its calibration, for example in one or more standard media as implemented in prior art.

Furthermore, still with reference to FIG. 7, the reference period P1 is also chosen to be long enough to measure the entire range of variability of the concentration S1 of VOC 40 in the indoor air of the office 4, and especially its maximum value and minimum value. In the example of FIG. 7, the concentration S1 of VOC 40 is a function of the occupancy rate O of the office 4 illustrated in FIG. 2 and varying between 0 occupant (minimum occupancy rate Omin) and 5 occupants (maximum occupancy rate Omax). Conventionally, the occupants gradually arrive in the morning, leave for lunch and come back in the afternoon before gradually going home. The occupancy rate is therefore minimal Omin at noon, in the morning before the arrival of the first occupant and in the evening after the departure of the last occupant. The occupancy rate is on the contrary maximal Omax during the morning and the afternoon. In the example of FIG. 7, the reference period P1 is thus chosen equal to one day, which is sufficient to measure the first concentration S1P1 when the occupancy rate is minimal Omin and maximal Omax. In general, the reference period P1 is preferably between one day and one month, preferably in the order of one week.

Still with reference to FIG. 7, the first concentration S1P1 of VOC 40 corresponds to a plurality of measurement points (represented by triangles in FIG. 7) spaced by a measurement pitch $\Delta t$. In this example, the measurement pitch $\Delta t$ is equal to 1 h, small enough to observe the temporal variation of the first concentration S1P1 and large enough to limit the size of the measured data. In general, the measurement pitch $\Delta t$ is preferably between 1 min and 4 h, depending on the physical medium and the physical or chemical quantity measured. The first concentration S2P1 of CO2 41 preferably comprises the same number of measurement points (represented by crosses in FIG. 7) measured at the same measurement time as for the first concentration S1P1 of VOC 40. In this example, the measurement points correspond to instantaneous values, but of course the measurement points could also correspond to values averaged over a time period, for example equal to the measurement pitch $\Delta t$.

With reference to FIG. 5, at the end of the measurement step E1, the first concentration S1P1 of VOC 40 and the first concentration S2P1 of CO2 41 are transmitted to the calculation module 3, and more precisely in the example of FIG. 5 to a first calculation unit 32 of the calculation module 3.

Figure 8:
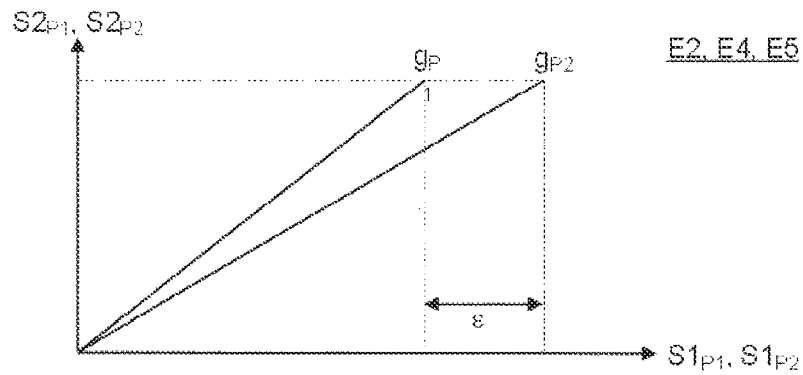
FIG. 8 is a schematic representation of the regression functions, for the reference period and for the test period, between the chemical signal of the sensor to be calibrated and that of the reference sensor of the calibration system of FIG. 2.

With reference to FIGS. 4, 5 and 8, the calibration method continues with a step of determining E2 a first regression function $g_{P1}$ defined as follows: $S2_{P1}=g_{P1}(S1_{P1})$. In other words, the first regression function $g_{P1}$ corresponds to the time course of the first concentration $S2_{P1}$ of CO2 41 as a function of the first concentration $S1_{P1}$ of VOC 40 over the reference period P1. A point of the first regression function $g_{P1}$ is thus obtained by a measurement point of the first concentration $S1_{P1}$ of VOC 40 and a measurement point of the first concentration $S2_{P1}$ of CO2 41 at the same measurement time. Such a first regression function $g_{P1}$ makes it possible to obtain the correlation relationship linking the first concentration $S1_{P1}$ of VOC 40 and the first concentration $S2_{P1}$ of CO2 41. Since the sensor to be calibrated 1 is deemed valid during the reference period P1, such a first regression function $g_{P1}$ illustrates the actual, accurate and fair correlation relationship existing between the concentration S2 of CO2 41 and the actual concentration of VOC 40, and thus serves as a control thereafter to evaluate the drift of the sensor to be calibrated 1 and correct the conversion function f. Preferably, the first regression function $g_{P1}$ is polynomial, preferably affine, preferably linear so as to be simple to determine and use thereafter.

With reference to FIG. 5, at the end of the determination step E2, the first regression function $g_{P1}$ is stored in the calculation module 3 and more precisely in the database 30.

With reference to FIGS. 6 and 7, the calibration method continues with a measurement step E3 similar to the measurement step E1 except that it is implemented during a test period P2 subsequent to the reference period P1. The concentration S1 of VOC 40 and the concentration S2 of CO2 41 measured during the test period P2 are respectively noted as "second concentration $S1_{P2}$ of VOC 40" and "second concentration $S2_{P2}$ of CO2 41".

Preferably, the test period P2 is implemented when the sensor to be calibrated 1 is likely to have drifted, for example between 1 month and 12 months after the reference period P1 or after its last calibration. However, of course the test period P2 could be implemented earlier to verify the correct operation of the sensor to be calibrated 1 or following an anomaly observed as examples. Like the reference period P1, the test period P2 is preferably chosen to be long enough to measure the entire range of variability of the concentration S1 of VOC 40 in the indoor air of the office 4, and especially its maximum value and minimum value. Preferably, the test period P2 is chosen to be of identical duration to the reference period P1 and with the same number of measurement points.

With reference to FIG. 6, as well as at the end of the measurement step E1, the second concentration $S1_{P2}$ of VOC 40 and the second concentration $S2_{P2}$ of CO2 41 are transmitted to the calculation module 3, and more precisely in the example of FIG. 6 to the first calculation unit 32.

With reference to FIGS. 6 and 8, the calibration method then comprises a step of determining E4 a second regression function $g_{P2}$ defined as follows: $S2_{P2}=g_{P2}(S1_{P2})$, similarly to the determination step E2. Like the first regression function $g_{P1}$, the second regression function $g_{P2}$ is preferably polynomial, preferably affine, more preferably linear so as to be simple to determine and use subsequently.

Still with reference to FIGS. 6 and 8, in a calculation step E5, a second calculation unit 33 of the calculation module 3 determines the deviation ε between the first regression function $g_{P1}$ transmitted by the database 30 and the second regression function gp2 transmitted by the first calculation unit 32.

In the example of FIG. 8, the deviation ε determined corresponds to the maximum difference observed between the first concentration $S1_{P1}$ and the second concentration $S1_{P2}$ of VOC 40 for a given concentration S2 and is expressed according to the following relationship: ε=Max $(|S1_{P1}-S1_{P2}|)/S1_{P1}$ such that $S2_{P1}=S2_{P2}$. Of course the deviation ε between the two regression functions $g_{P1}$, $g_{P2}$ could be determined in other ways, for example at each measurement point rather than at the measurement point where the deviation ε is maximum.

Advantageously, such a deviation ε is representative of the possible drift of the sensor to be calibrated 1. Indeed, among the four measured concentrations $S1_{P1}$, $S1_{P2}$, $S2_{P1}$, $S2_{P2}$, only the second concentration $S1_{P2}$ of VOC 40 is not deemed valid, so that the observed deviation ε is only due to the drift of the sensor to be calibrated 1 between the reference period P1 and the test period P2. It is noted here the necessity of the presence of a reference sensor 2 which serves to know accurately and reliably the composition of the indoor air of the office 4 which is a priori different for the reference period P1 and the test period P2. A comparison between the first concentration $S1_{P1}$ and the second concentration $S2_{P1}$ of VOC 40 would indeed not be relevant because the measurements would not be carried out in a physical medium of identical chemical composition. Indeed, as an example, one of the occupants could be absent during the test period P2, reducing the maximum occupancy rate Omax and thus the amount of VOC 40 in the indoor air of the office 4. Thus, it is also noted the necessity to have a reference sensor 2 deemed valid at any time, because a drift of the reference sensor 2 would make the deviation c unrepresentative of the drift of the sensor to be calibrated 1.

With reference to FIG. 6, the calibration method ends with a determination step E6 during which, if the deviation c is greater than a minimum deviation $\varepsilon_{ref}$, a third calculation unit 34 of the calculation module 3 determines an optimized conversion function f* for the sensor to be calibrated 1, so as to correct the drift. The minimum deviation $\varepsilon_{ref}$ corresponds to the threshold above which the drift is considered not negligible. Preferably, the minimum deviation $\varepsilon_{ref}$ comes from the database 30 and is between 0.01 and 0.1, preferably in the order of 0.05, which makes it possible to avoid any significant drift while avoiding having to carry out an irrelevant micro-correction. In practice, the value of the minimum deviation $\varepsilon_{ref}$ is adjusted by feedback.

In the example of FIG. 6, the determination step E6 is implemented by calculating the optimized conversion function f* as follows: $g_{P2}(f^*(U_{P2}))=g_{P1}(S1_{P1})$, noting UP2 the electrical conductivity of the metal oxide layer of the sensor to be calibrated 1 measured during the test period P2 and which is related to the second concentration S1P2 of VOC 40 by the relationship: $S1_{P2}=f(U_{P2})$. In other words, the optimized conversion function f* is calculated by seeking equality $g_{P2}=g_{P1}$, that is, the two regression functions $g_{P1}$, $g_{P2}$ correspond to a polynomial function with the same coefficients.

To summarize, the calibration method according to the invention makes it possible to determine an optimized conversion function f* for the sensor to be calibrated 1 base on the deviation ε between a first regression function $g_{P1}$ for a reference period P1 in which the sensor to be calibrated 1 is deemed valid and a second regression function $g_{P2}$ for a test period P2 in which the sensor to be calibrated 1 has potentially drifted. The two regression functions $g_{P1}$, $g_{P2}$ are calculated by relating the physical quantities measured by the sensor to be calibrated 1 and a reference sensor 2, deemed valid at any time, in a same physical medium 4. The reference sensor 2 thus makes it possible to know the composition of the physical medium 4 at any time and thus to evaluate the drift of the sensor to be calibrated 1.

Furthermore, in the example of FIGS. 2 and 3, the calibration method is carried out in the indoor air of an office 4 by means of a calibration system comprising a semiconductor sensor 1 of VOC 40, an infrared sensor 2 of CO2 41 and a microprocessor 3, but of course the calibration method can be carried out in any physical medium and by means of a sensor to be calibrated 1 being in the form of any non-selective chemical sensor, the reference sensor 2 being chosen as a function of the sensor to be calibrated 1 and of the physical medium 4 and the calculation module 3 comprising at least a database 30 and a computer 31.

Figure 9:
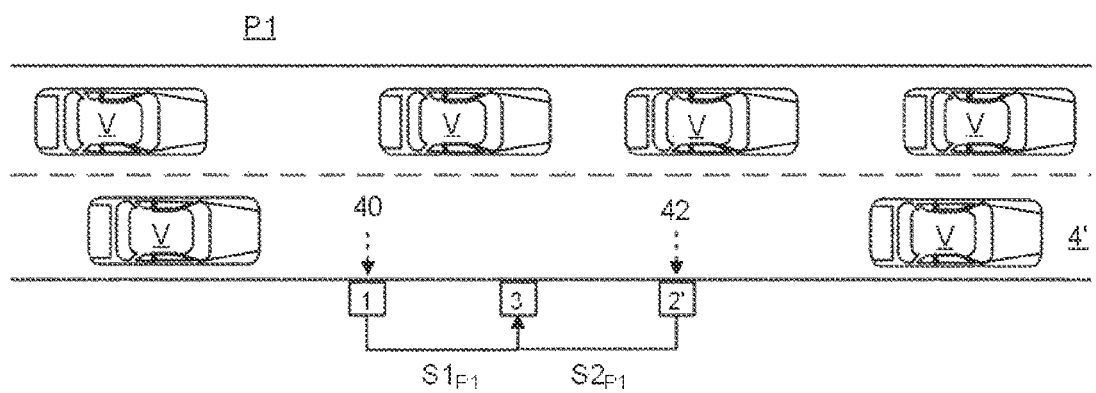
FIG. 9 is a functional schematic representation of the calibration system according to another embodiment of the invention and FIG. 10 is a representation of the physical signals of the sensor to be calibrated and the reference sensor of the calibration system of FIG. 9, during the reference period and during the test period.
Figure 10:
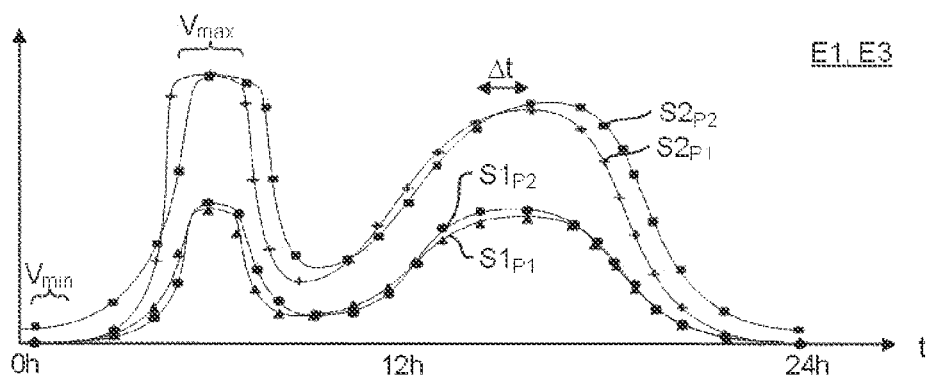

Thus, in the example of FIGS. 9 and 10 illustrating another embodiment of the invention, the calibration method is implemented in proximity to a road 5 where vehicles V are travelling. The sensor to be calibrated 1 is as previously in the form of a semiconductor VOC sensor 40. The reference sensor 2 is in the form of a sound intensity sensor 42 of the road 5. Such a sound intensity sensor 42 is advantageously self-calibrated and performs accurate measurements, which makes it a suitable reference sensor. Moreover, the sound intensity 42 is a function of the traffic of vehicles V on the road 5 as well as the concentration of VOC 40 emitted in proximity to the road 5, so that the physical quantities measured by the sensor to be calibrated 1 and the reference sensor 2 are correlated. Conventionally, with reference to FIG. 10, the traffic of vehicles V has a peak in the morning corresponding to the trip to work and a more extended peak in the afternoon and evening corresponding to the trip home from work. The traffic of vehicles V is thus maximal Vmax in the morning and minimal Vmin very early in the morning. In the example of FIG. 10, the reference period P1 is thus chosen equal to one day as in the example of FIGS. 2 and 3, because such a reference period P1 is sufficient to measure the first concentration S1P1 when the traffic of vehicles V is minimal Vmin and maximal Vmax.

A calibration system comprising a single sensor to be calibrated 1 and a single reference sensor 2 has been previously described, but of course the calibration system could comprise several sensors to be calibrated 1 each configured to be calibrated by a reference sensor 2. Preferably, such a calibration system comprises a single reference sensor 2 allowing the calibration of each sensor to be calibrated 1 in order to limit the overall size. Thus, by way of example, using the embodiment of the invention in FIG. 10, the sensor to be calibrated 1 in the form of a semiconductor VOC sensor 40 could be replaced by an array of sensors to be calibrated 1 comprising a semiconductor sensor and an electrochemical VOC sensor 40 as well as a carbon monoxide and nitrogen oxide sensor. Such a sensor array has the advantage of measuring the air quality in proximity to the road more accurately than a semiconductor VOC sensor 40 alone. The reference sensor 2 remains unchanged and is in the form of a sound intensity sensor 42, with the sound intensity 42 emitted by the traffic being related to the amount of VOCs produced, but also to those of carbon monoxide and nitrogen oxide.

For such a calibration system, the calibration method is implemented by measuring a first chemical signal S1P1 and a second chemical signal S1P2 from each sensor to be calibrated 1. A first regression function $g_{P1}$ and a second regression function $g_{P2}$ are then calculated for each sensor to be calibrated 1. A deviation $\varepsilon$ is then determined for each sensor to be calibrated 1 to determine the required calibration for each independently.

The invention claimed is:

1. A method for calibrating at least one sensor to be calibrated by means of at least one reference sensor, the at least one sensor to be calibrated and the at least one reference sensor being in contact with a same chemical medium, said at least one sensor to be calibrated being configured to determine a chemical signal (S1) of the amount of a group of chemical compounds in said chemical medium, said at least one reference sensor being configured to determine a reference signal whose temporal variation is correlated to that of said chemical signal (S1), said at least one sensor to be calibrated comprising:
an element for measuring an electrical signal (U), which is a function of the amount of said group of chemical compounds in said chemical medium, and
an element for calculating said chemical signal (S1) based on a conversion function (f) specific to said at least one sensor to be calibrated and configured to associate the corresponding chemical signal (S1) with said measured electrical signal (U) according to the following relationship: S1=f(U),
said method for calibrating said at least one sensor to be calibrated by means of said at least one reference sensor comprising:
a step of measuring, during a reference period, a first chemical signal ($S1_{P1}$) by means of said at least one sensor to be calibrated and a first reference signal ($S2_{P1}$) by means of said at least one reference sensor,
a step of determining a first regression function ($g_{P1}$) defined as follows: $S2_{P1}=g_{P1}(S1_{P1})$,
at least one step of measuring, during a test period subsequent to the reference period, a second chemical signal ($S1_{P2}$) by means of said at least one sensor to be calibrated and a second reference signal ($S2_{P2}$) by means of said at least one reference sensor,
at least one step of determining a second regression function ($g_{P2}$) defined as follows: $S2_{P2}=g_{P2}(S1_{P2})$,
at least one step of calculating a deviation ($\varepsilon$) between the first regression function ($g_{P1}$) and the second regression function ($g_{P2}$) and
when the deviation ($\varepsilon$) is greater than a reference deviation, at least one step of determining an optimized conversion function (f*) so that the second regression function ($g_{P2}$) is equal to the first regression function ($g_{P1}$) to enable calibrating said at least one sensor to be calibrated.

2. The calibration method according to claim 1, implemented for a plurality of test periods subsequent to the reference period, said method comprising for each test period:
a step of measuring, during the test period, a second chemical signal ($S1_{P2}$) by means of the at least one sensor to be calibrated and a second reference signal ($S2_{P2}$) by means of the at least one reference sensor,
a step of determining a second regression function ($g_{P2}$) defined as follows: $S2_{P2}=g_{P2}(S1_{P2})$,
a step of calculating a deviation between the first regression function ($g_{P1}$) and the second regression function ($g_{P2}$) and
when the deviation is greater than a reference deviation, a step of determining an optimized conversion function so that the second regression function ($g_{P2}$) is substantially equal to the first regression function ($g_{P1}$), so as to calibrate said at least one sensor to be calibrated.

3. The calibration method according to claim 1, wherein the at least one sensor to be calibrated is in the form of a VOC sensor.

4. The calibration method according to claim 1, wherein the at least one reference sensor is in the form of a carbon dioxide sensor.

5. The calibration method according to claim 1, wherein the at least one reference sensor is in the form of a sound intensity sensor.

6. The calibration method according to claim 1, wherein the reference period is between one day and one month.

7. The calibration method according to claim 1, wherein the deviation ($\varepsilon$) holds the following relationship: $\varepsilon=\mathrm{Max}(|S1_{P1}-S1_{P2}|)/S1_{P1}$ such that $S2_{P1}=S2_{P2}$.

8. The calibration method according to claim 1, wherein, the second chemical signal ($S1_{P2}$) being determined based on a second electrical signal ($U_{P2}$), the optimized conversion function (f*) holds the following relationship: $g_{P2}(f^*(U_{P2}))=g_{P1}(S1_{P1})$.

9. A calibration system for implementing the calibration method according to claim 1, said system comprising at least one sensor to be calibrated and at least one reference sensor configured to be in contact with a same chemical medium and a calculation module connected to the at least one sensor to be calibrated and to the at least one reference sensor, said at least one sensor to be calibrated being configured to determine a chemical signal (S1) of the amount of a group of chemical compounds in said chemical medium, in particular a first chemical signal ($S1_{P1}$) during a reference period and a second chemical signal ($S1_{P2}$) during a test period, said at least one reference sensor being configured to determine a reference signal whose temporal variation is correlated to that of said chemical signal (S1) in particular a first reference signal ($S2_{P1}$) during said reference period and a second reference signal ($S2_{P2}$) during said test period, said at least one sensor to be calibrated comprising:

an element for measuring an electrical signal (U), which is a function of the amount of said group of chemical compounds in said chemical medium, and an element for calculating said chemical signal (S1) based on a conversion function (f) specific to said at least one sensor to be calibrated and configured to associate the corresponding chemical signal (S1) with said measured electrical signal (U) according to the following relationship: $S1=f(U)$, said calculation module being configured to:

determine a first regression function ($g_{P1}$) and a second regression function ($g_{P2}$) defined as follows: $S2_{P1}=g_{P1}(S1_{P1})$ and $S2_{P2}=g_{P2}(S1_{P2})$ calculate a deviation between the first regression function ($g_{P1}$) and the second regression function ($g_{P2}$) and when the deviation is greater than a reference deviation, determine an optimized conversion function so that the second regression function ($g_{P2}$) is equal to the first regression function ($g_{P1}$) to enable calibrating the at least one sensor to be calibrated.

10. A computer program implementing the calibration method according to claim 1 when said program is run on a computer.

* * * * *